(12) United States Patent
Zhong et al.

(10) Patent No.: US 12,140,365 B2
(45) Date of Patent: *Nov. 12, 2024

(54) AIR SANITATION DEVICE FOR REFRIGERATOR AND REFRIGERATOR

(71) Applicant: BSH Hausgeraete GmbH, Munich (DE)

(72) Inventors: Wei Zhong, Nanjing (CN); Haiqing Zhou, Nanjing (CN); Chenli Hu, Nanjing (CN)

(73) Assignee: BSH Hausgeraete GmbH, Munich (DE)

( * ) Notice: Subject to any disclaimer, the term of this patent is extended or adjusted under 35 U.S.C. 154(b) by 402 days.

This patent is subject to a terminal disclaimer.

(21) Appl. No.: 17/564,420

(22) Filed: Dec. 29, 2021

(65) Prior Publication Data

US 2022/0205701 A1   Jun. 30, 2022

(30) Foreign Application Priority Data

Dec. 29, 2020 (CN) ......................... 202011588466.X

(51) Int. Cl.
*F25D 17/04* (2006.01)
*A61L 9/015* (2006.01)
(Continued)

(52) U.S. Cl.
CPC ............ *F25D 17/042* (2013.01); *A61L 9/015* (2013.01); *A61L 9/20* (2013.01); *A61L 9/22* (2013.01);
(Continued)

(58) Field of Classification Search
CPC .. F25D 17/042; F25D 27/00; F25D 2317/041; F25D 2317/0415; F25D 2317/0416; F25D 2317/0417; F25D 17/062; F25D 11/00; A61L 9/015; A61L 9/20; A61L 9/22; A61L 2209/111;
(Continued)

(56) References Cited

U.S. PATENT DOCUMENTS

| 7,993,589 B1 * | 8/2011 | Shigemoto ................ A61L 9/01 422/122 |
| 10,371,431 B2 | 8/2019 | Seo |

(Continued)

FOREIGN PATENT DOCUMENTS

| CN | 105148313 A | 12/2015 |
| CN | 110251704 A | 9/2019 |

(Continued)

OTHER PUBLICATIONS

Machine-generated English translation of JP 2020041751 A, published Mar. 19, 2020.*

*Primary Examiner* — Frank M Lawrence, Jr.
(74) *Attorney, Agent, or Firm* — Laurence A. Greenberg; Werner H. Stemer; Ralph E. Locher

(57) ABSTRACT

A refrigerator has an air sanitation device. The air sanitation device includes: a housing; an air channel located in the housing and having an air inlet and an air outlet; a fan located in the air channel, to force air to enter the air channel from the air inlet, and then be discharged out of the air channel from the air outlet; and an air detection device and/or an air purification device located between the air inlet and an inlet of the fan.

13 Claims, 6 Drawing Sheets

(51) Int. Cl.
*A61L 9/20* (2006.01)
*A61L 9/22* (2006.01)
*B01D 46/00* (2022.01)
*B01D 46/42* (2006.01)
*B01D 46/46* (2006.01)
*B01D 53/26* (2006.01)
*F25D 27/00* (2006.01)

(52) U.S. Cl.
CPC ..... *B01D 46/0049* (2013.01); *B01D 46/4254* (2013.01); *B01D 46/46* (2013.01); *B01D 53/266* (2013.01); *F25D 27/00* (2013.01); *A61L 2209/111* (2013.01); *A61L 2209/12* (2013.01); *A61L 2209/14* (2013.01); *A61L 2209/212* (2013.01); *B01D 2273/30* (2013.01); *F25D 2317/041* (2013.01)

(58) Field of Classification Search
CPC ............. A61L 2209/12; A61L 2209/14; A61L 2209/212; B01D 46/0049; B01D 46/4254; B01D 46/46; B01D 53/266; B01D 2273/30

USPC ............................... 96/223, 226, 417; 55/418
See application file for complete search history.

(56) References Cited

U.S. PATENT DOCUMENTS

| | | | |
|---|---|---|---|
| 11,815,302 B2* | 11/2023 | Hu | F25D 17/042 |
| 2012/0181911 A1 | 7/2012 | Kim et al. | |
| 2014/0245771 A1* | 9/2014 | Kim | F25D 27/00 502/1 |
| 2017/0234598 A1 | 8/2017 | Yun et al. | |
| 2019/0083674 A1* | 3/2019 | Jeong | A61L 9/205 |
| 2020/0237951 A1 | 7/2020 | Lee et al. | |
| 2020/0386466 A1* | 12/2020 | Jeong | F25D 29/00 |
| 2022/0202983 A1* | 6/2022 | Hu | F25D 17/042 |
| 2022/0205702 A1* | 6/2022 | Liu | B01D 46/46 |

FOREIGN PATENT DOCUMENTS

| | | |
|---|---|---|
| CN | 110878998 A | 3/2020 |
| EP | 2144021 A1 | 1/2010 |
| JP | 2020041751 A | 3/2020 |

* cited by examiner

AIR SANITATION DEVICE FOR REFRIGERATOR AND REFRIGERATOR

CROSS-REFERENCE TO RELATED APPLICATION

This application claims the priority, under 35 U.S.C. § 119, of Chinese Patent Application CN 202011588466.X, filed Dec. 29, 2020; the prior application is herewith incorporated by reference in its entirety.

FIELD AND BACKGROUND OF THE INVENTION

Embodiments of the present invention relate to an air sanitation device for a refrigerator and a refrigerator.

Chinese patent application CN110878998A discloses a refrigerator, including a storage compartment having a front opening, a door for closing the storage compartment, and an air sanitation device fixed to a top wall of the storage compartment. The air sanitation device includes a housing and an air detection device and/or an air purification device located in the housing.

Chinese patent application CN105148313A discloses a sterilization and deodorization device for a refrigerator. The sterilization and deodorization device includes a housing provided with an airflow channel, a sterilization module located in the airflow channel, and a deodorization filtering module filled with sepiolite and located downstream of the sterilization module. The sterilization and deodorization device further includes an LED light bar, which is configured to make a ray of light emitted by the LED light bar exit through a central panel of a cover body of the housing, thereby integrating functions of sterilization, deodorization, and illumination.

SUMMARY OF THE INVENTION

An objective of embodiments of the present invention is to provide an improved air sanitation device for a refrigerator and a refrigerator.

Another objective of the embodiments of the present invention is to provide an air sanitation device with more reliable performance for a refrigerator and a refrigerator.

An aspect of the embodiments of the present invention relates to an air sanitation device for a refrigerator, including: a housing; an air channel located in the housing, and including an air inlet and an air outlet; a fan located in the air channel, to force air to enter the air channel from the air inlet, and then be discharged out of the air channel from the air outlet; and an air detection device and/or an air purification device located between the air inlet and an inlet of the fan.

In an implementation in which the air detection device is located between the fan and the air inlet, the air detection device may obtain more accurate sanitation parameters of to-be-detected ambient air, thereby helping improve the reliability of the air sanitation device. In an implementation in which the air purification device being disposed between the fan and the air inlet, air is purified before entering the fan, thereby helping reduce an adverse effect of the air entering the air channel from the outside on the fan and devices disposed downstream of the fan.

In a possible embodiment, the air detection device includes a gas sensor fixed to a circuit board.

In a possible embodiment, the air channel is configured to enable air to flow along a side of the circuit board to which the gas sensor is fixed, and a direction that the inlet of the fan faces is opposite to a direction in which the gas sensor protrudes from the circuit board.

In a possible embodiment, the air sanitation device includes a pair of boundary walls in opposite arrangement to define at least a part of the air channel, the gas sensor protrudes from the circuit board toward a first boundary wall of the pair of boundary walls, the inlet of the fan faces a second boundary wall of the pair of boundary walls, and the gas sensor is closer to the first boundary wall than the inlet of the fan. The first boundary wall and/or the second boundary wall may be formed by corresponding parts of the housing or other components located in the housing, such as a partition member or a carrying plate.

In a possible embodiment, the first boundary wall is located above the second boundary wall, the gas sensor protrudes upward from the circuit board toward the first boundary wall, the inlet of the fan faces downward the second boundary wall, and an upper end of the gas sensor is higher than the inlet of the fan.

In a possible embodiment, the gas sensor includes a sensing element enclosed in a cavity and a permeable layer covering an inlet of the cavity, and the permeable layer is higher than the inlet of the fan.

In a possible embodiment, the permeable layer is higher than at least a part of the air inlet.

In a possible embodiment, the circuit board is fixed to a carrying plate, a gap is disposed between the circuit board and the carrying plate, and the gap is closed by a closing portion at an upstream side of the circuit board close to the air inlet.

In a possible embodiment, the air sanitation device includes the first boundary wall and the second boundary wall in opposite arrangement to define the air channel. The air detection device and/or the air purification device are fixed to the second boundary wall, and the air inlet is configured to enable air to enter the air inlet and then flow obliquely toward the first boundary wall.

In a possible embodiment, the inlet of the fan faces the second boundary wall, so that the air flows obliquely downward at least in some segments between the air detection device and/or the air purification device and the inlet of the fan.

In a possible embodiment, the housing includes an upper wall, a lower wall, and a side wall. The side wall includes an oblique portion inclined downward, the air inlet is located on the oblique portion, and the inlet of the fan is open downward.

In a possible embodiment, the air purification device includes: an air filter located between the air inlet and the fan; and/or a sterilization device located between the fan and the air outlet.

In a possible embodiment, the air sanitation device includes a partition member and an illumination device that are located in the housing, the housing includes a light outlet, the air detection device and/or the air purification device are located at a first side of the partition member away from the light outlet, and the illumination device is located at a second side of the partition member facing the light outlet.

Another aspect of the embodiments of the present invention relates to a refrigerator, including a storage compartment and the air sanitation device according to any one of the foregoing embodiments, where the air sanitation device is located in the storage compartment.

In a possible embodiment, the air sanitation device is fixed to a top wall of the storage compartment, and the air channel is configured to enable air to be discharged out from a rear part of the housing obliquely downward.

Other features of the present invention are shown in the claims, accompanying drawings, and description of the accompanying drawings. The features and feature combinations described in the foregoing description and the features and feature combinations described in the description of the following accompanying drawings and/or simply shown in the accompanying drawings can not only be presented by the described combination manners, but also be presented by other combinations or separately without departing from the scope of the present invention. The embodiments of the present invention that are not described and not specifically shown in the accompanying drawings but can be thought of from the detailed description of the embodiments and that can be obtained from combinations of various features shall be considered to be included and disclosed.

Although the invention is illustrated and described herein as embodied in an air sanitation device for a refrigerator and a refrigerator, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
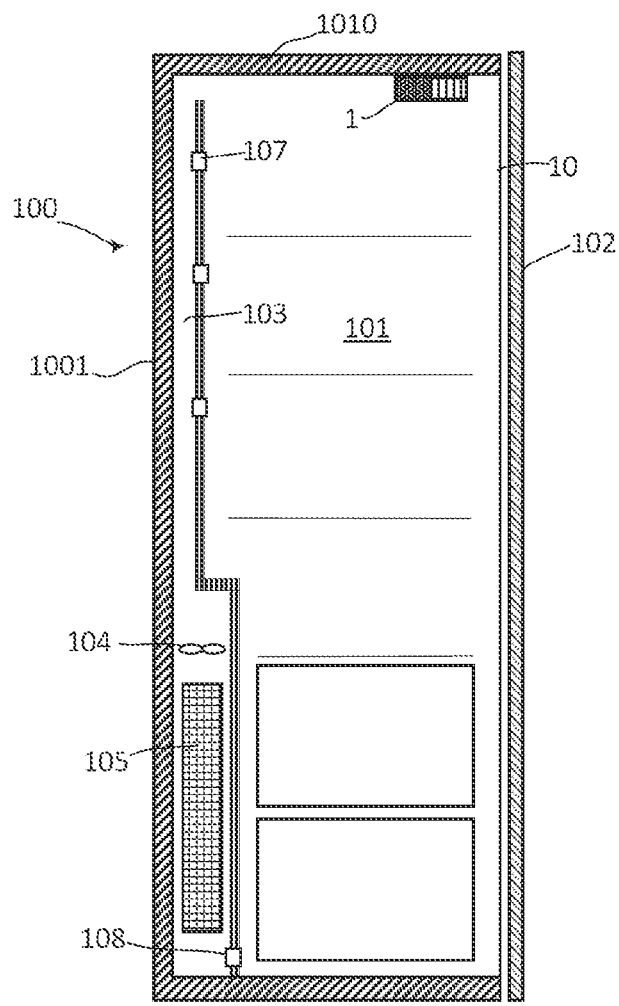
FIG. 1 is a schematic cross-sectional view of a refrigerator having an air sanitation device according to an embodiment of the present invention.

Referring now to the figures of the drawings in detail and first, particularly to FIG. 1 thereof, there is shown a refrigerator 100 which includes a storage compartment 101 having a front opening 10 and a door 102 for closing the storage compartment 101.

In an embodiment, a top wall 1010 of the storage compartment 101 may be a top wall of a refrigerator body 1001 of the refrigerator 100. The storage compartment 101 may extend from an upper part of the refrigerator body 1001 to a lower part, or another storage compartment is further disposed in a lower part of the storage compartment 101. It should be understood that, in an alternative embodiment, it is possible that another storage compartment is further provided in an upper part of the storage compartment 101.

The refrigerator 100 may include an air duct 103 for conveying cooled air to the storage compartment 101. The air duct 103 may be disposed in a rear part and/or a top part of the storage compartment 101. In the embodiment shown in FIG. 1, the air duct 103 is disposed in the rear part of the storage compartment 101.

The refrigerator 100 may include an air duct fan 104 for forming forced air circulation in a storage region of the storage compartment 101 and the air duct 103. For example, during operation of the air duct fan 104, air in the air duct 103 enters the storage region of the storage compartment 101 through an air vent 107, and the air in the storage region of the storage compartment 101 returns to the air duct 103 from an air return vent 108.

An evaporator 105 may be disposed in the air duct 103. In other embodiments, cold air in the air duct 103 also comes from another storage compartment.

The refrigerator 100 includes an air sanitation device 1 for detecting at least one air sanitation related parameter in the storage compartment 101 and/or purifying air in the storage compartment 101. In some embodiments, the air sanitation device 1 is merely used for detecting the air sanitation related parameter in the storage compartment 101. In some other embodiments, the air sanitation device 1 has a purification device, such as any device adapted to perform sterilization and deodorization. In still other embodiments, the air sanitation device 1 may include an air detection device and an air purification device.

Figure 2:
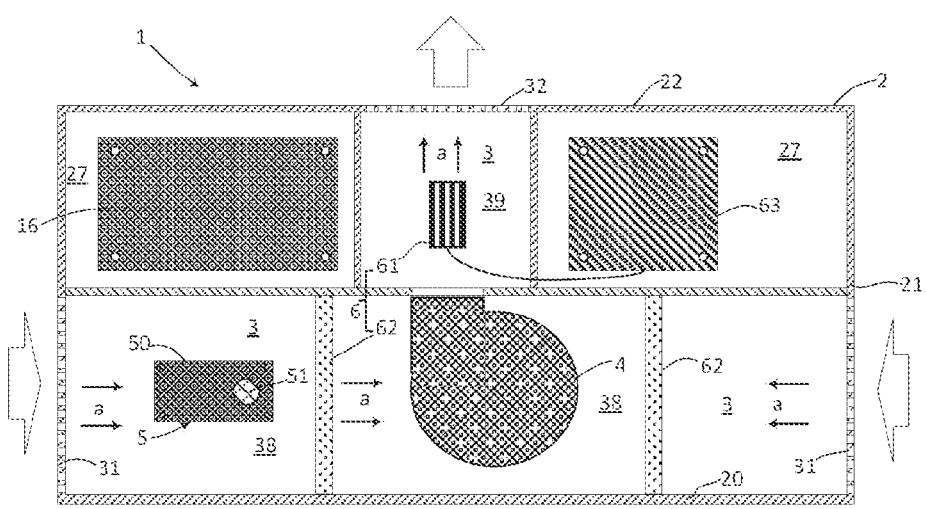
FIG. 2 is a schematic cross-sectional view of the air sanitation device according to an embodiment of the present invention.

In an exemplary example, as shown in FIG. 2, the air sanitation device 1 may include a housing 2, an air channel 3 located in the housing 2, and an air detection device 5 and an air purification device 6 located in the air channel 3.

Air from outside (for example, the storage compartment 101) may enter the air channel 3 through an air inlet 31, and be discharged out of the air channel 3 through an air outlet 32. The air inlet 31 and the air outlet 32 may be formed in the housing 2.

The air sanitation device 1 includes a fan 4 located in the air channel 3, to force the air from the outside to enter the air channel 3 and be discharged out of the housing 2 after flowing through the air detection device 5 and the air purification device 6. A flow direction of the air in the air channel 3 may be shown by an arrow a.

The air detection device 5 may be configured to detect at least one gas parameter in the storage compartment 101. For example, the gas parameter may include whether there are one or more types of gases, and/or contents or concentrations of ingredients of one or more types of gases. The air detection device 5 may be further configured to detect germ related parameters in air.

In an embodiment, the air detection device 5 detects concentrations of total volatile organic compounds (TVOCs) in the storage compartment 101.

The air detection device 5 may include a first circuit board 50 and a gas sensor 51 fixed to the first circuit board 50. The gas sensor 51 may be, but is not limited to, a metal-oxide semiconductor gas sensor, and the gas sensor may include a semiconductor sensing element and a heater for heating the semiconductor sensing element.

The air purification device 6 may include any one or more of an air filter, an ultraviolet sterilization device, an ion generation device, an ozone generation device, and the like. Different purification devices may be integrated into one module or be separately arranged.

The air purification device 6 may be located downstream of the air detection device 5 and be arranged in the air channel 3.

Therefore, the air purification device 6 may be located between the air detection device 5 and the air outlet 32.

In an exemplary embodiment, the air purification device 6 includes an ion generator 61, and the ion generator 61 is configured to release ions into the air channel 3. A power supply unit 63 for supplying power to the ion generator 61 is located in the housing 2.

The air purification device 6 may further include an air filter 62. The air filter 62 may be a physical and/or chemical filter, such as an adsorption filter or an enzyme filter (for example, Pt filter).

In an embodiment, when the air sanitation device 1 is arranged in a non-freezing compartment, the air filter 62 is arranged upstream of the ion generator 61, to filter impurities in air and reduce humidity of air flowing through the ion generator 61. It is found in experiments that, this can effectively reduce foreign substances gathered on a tip of the ion generator 61, thereby significantly reducing a possibility that crystals are generated on the tip of the ion generator 61 due to the impurities and water vapor in the air adhering to the tip and then productions of ions and ozone are reduced. Therefore, sterilization efficiency of the air purification device 6 may be improved.

In an embodiment, the air filter 62 is arranged upstream of the fan 4, and the ion generator 61 is arranged downstream of the fan 4. In an implementation having the air detection device 5, the air filter 62 is located between the air detection device 5 and the ion generator 61.

The air sanitation device 1 may include a control unit 16 operatively connected to the air detection device 5. The control unit 16 is adapted to receive a signal from the air detection device 5. The control unit 16 may alternatively be configured to be adapted to send an instruction to the air detection device 5.

The control unit 16 may be operatively connected to the fan 4. The fan 4 may operate or stop operating based on the instruction of the control unit 16.

The control unit 16 may be operatively connected to the power supply unit 63. The power supply unit 63 may supply power to the ion generator 61 based on the instruction of the control unit 16.

A baffle wall 161 around the control unit 16 and a baffle wall 631 around the power supply unit 63 are disposed in the housing 2, to reduce a chance that air is in contact with the control unit 16 and the power supply unit 63. In an embodiment, the control unit 16 and the power supply unit 63 are disposed adjacent to a rear wall 22.

As shown in FIG. 2, the air channel 3 includes a first channel segment 38 located between the air inlet 31 and the fan 4, and a second channel segment 39 located between the fan 4 and the air outlet 32. The first channel segments 38 extend transversely toward the fan 4, and the second channel segment 39 extends toward the rear wall 22 in a front-to-rear direction.

In an embodiment, an air inlet 31 is disposed on each side wall 21, a pair of first channel segments 38 merge at an inlet 41 of the fan 4, and the second channel segment 39 extends rearward from an outlet 42 of the fan 4.

The baffle walls 631 and 161 are disposed between the first channel segments 38 and the rear wall 22, to define mounting regions 27 between the rear wall 22 and the baffle walls 631 and 161, at least one electric component is disposed in the mounting regions 27, and the electric component is electrically coupled to the air detection device 5 and/or the air purification device 6. The electric component may include the control unit 16 and/or the power supply unit 63 electrically coupled to the air detection device 5 and/or the air purification device 6.

The housing 2 may include two mounting regions 27, and the second channel segment 39 is located between the two mounting regions 27 in a transverse direction of the air sanitation device 1.

Therefore, the air channel 3 extends from front parts of two sides of the housing 2 toward the middle of the housing 2, and is discharged toward a rear part of the housing 2 after passing through the fan 4. The control unit 16 and the power supply unit 63 are located at two sides of the second channel segment 39 of the air channel 3.

Figure 3:
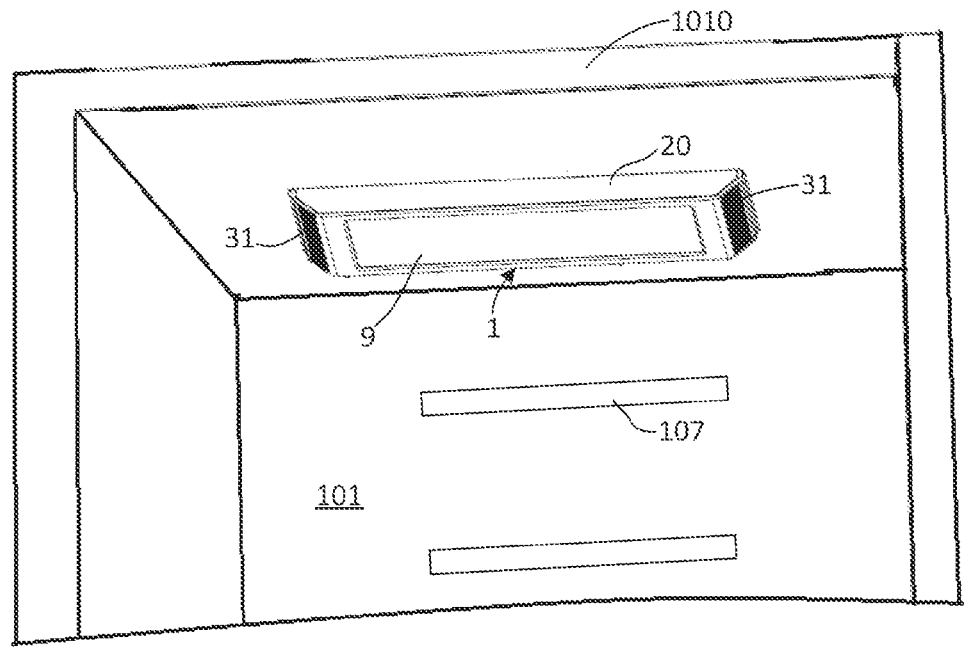
FIG. 3 is a schematic partial three-dimensional view of the refrigerator having the air sanitation device according to an embodiment of the present invention.
Figure 4:
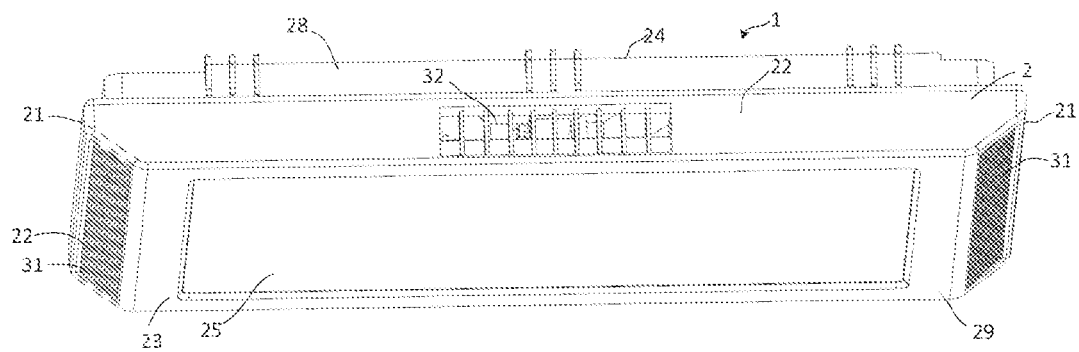
FIG. 4 is a three-dimensional view of the air sanitation device according to an embodiment of the present invention.
Figure 5:
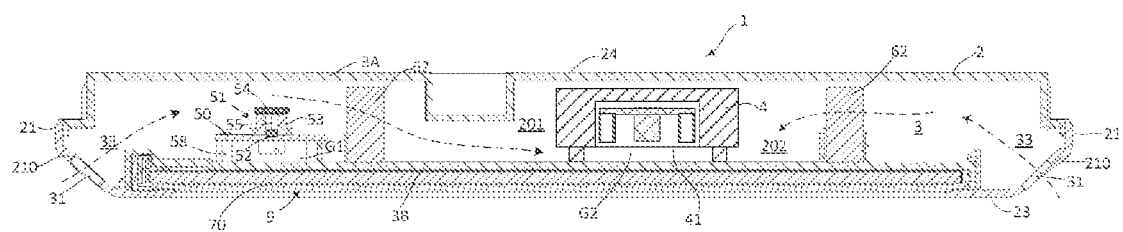
FIG. 5 is a schematic cross-sectional view of the air sanitation device according to an embodiment of the present invention.

FIG. 3 is a schematic partial three-dimensional view of a refrigerator having an air sanitation device according to an embodiment of the present invention. FIG. 4 is a schematic three-dimensional view of an air sanitation device according to an embodiment of the present invention. FIG. 5 is a schematic cross-sectional view of an air sanitation device. As shown in FIG. 3 to FIG. 5, a housing 2 includes a front wall 20 facing a front opening 10, a rear wall 22 facing a rear part of a storage compartment 101, a bottom wall 23, an upper wall 24, and a pair of side walls 21.

The housing 2 may include a first housing 28 and a second housing 29. An air channel 3 is located between the first housing 28 and the second housing 29.

An air inlet 31 is located at a side part of the housing 2. The air inlet 31 may be located at a single side or two sides of the housing 2. An air outlet 32 is located at a rear part of the housing 2. Air from the storage compartment 101 enters the housing 2 from two sides of the air sanitation device 1, and finally returns to the storage compartment 101 from the rear part of the housing 2.

The housing 2 may be flat, and the air channel 3 in the housing 2 is also flat. A pair of boundary walls in opposite arrangement define at least a part of opposite boundaries of the air channel 3. In this embodiment that a first boundary wall 3A is located above a second boundary wall 3B in the pair of boundary walls, the first boundary wall 3A may also be referred to as an upper boundary wall, and the second boundary wall 3B may also be referred to as a lower boundary wall.

In an embodiment, the first boundary wall 3A is formed by the upper wall 24 of the housing 2.

In an embodiment, the second boundary wall 3B is located between the upper wall 24 and the bottom wall 23 of the housing 2. The second boundary wall 3B may be formed by a carrying member 7 for carrying an air detection device 5 and/or an air purification device 6. It should be understood that, in other embodiments of the present invention, the second boundary wall 3B may alternatively be formed by, for example, the bottom wall 23.

A plurality of air inlets 31 are distributed at intervals on the side walls 21. The air inlets 31 may be distributed over most of lengths of the side walls 21 in a front-to-rear direction, and even some air inlets 31 may overlap a control unit 16 or a power supply unit 63 of an ion generator 61.

In an implementation, as shown in FIG. 3 to FIG. 5, the side walls 21 include an oblique portion 210 that makes the housing 2 gradually contract in a width direction of the storage compartment 101 in a top-to-bottom direction, and the air inlet 31 is located at the oblique portion 210. Therefore, when the air sanitation device 1 is mounted on a top part of the storage compartment 101, the air inlet 31 is obliquely downward, which helps air enter the air sanitation device 1.

The air channel 3 includes an introduction segment 33 through which air flows obliquely upward. After entering the air inlet 31, the air flows obliquely upward toward the upper wall 24 of the housing 2. An inlet of a fan 4 is lower than the upper wall 24, to drive air to flow obliquely downward.

In an embodiment, the air channel 3 is configured to enable air to flow along a side of a first printed circuit board 50 to which a gas sensor 51 is fixed, and a direction that an inlet 41 of the fan 4 faces is opposite to a direction in which the gas sensor 51 protrudes from the circuit board 50.

In an embodiment, in a pair of opposite boundary walls of the air channel 3, the gas sensor 51 protrudes from the first circuit board 50 toward the first boundary wall 3A, the inlet 41 of the fan 4 faces the second boundary wall 3B, and the gas sensor 51 is closer to the first boundary wall 3A than the inlet 41 of the fan 4.

When the air sanitation device 1 is mounted on a top wall 1010 of the storage compartment 101, the gas sensor 51 protrudes from the first printed circuit board 50 toward the upper boundary wall of the air channel 3, and the inlet 41 of the fan 4 faces the lower boundary wall which defines a lower boundary of the air channel 3. The gas sensor 51 is closer to the upper boundary wall of the air channel 3 than the inlet 41 of the fan 4.

In an embodiment, the gas sensor 51 may include a sensing element 52 fixed to the circuit board 50, a sensor cover 53 protruding from the circuit board 50 and having an accommodating cavity for accommodating the sensing element 52, and a permeable layer 54 for covering an inlet of the accommodating cavity. The permeable layer 54 covers an inlet of a free end of the sensor cover 53, to allow air to pass through the permeable layer 54 to enter the sensor cover 53 and be in contact with the sensing element 52. The permeable layer 54 may be substantially parallel to the first circuit board 50 or the second boundary wall 3B of the air channel 3.

The permeable layer 54 is higher than the inlet 41 of the fan 4, so that the permeable layer 54 is closer to the first boundary wall 3A of the air channel 3 than the inlet 41 of the fan 4.

As shown in FIG. 5, at least a part of the air inlet 31 is lower than the permeable layer 54. For example, the permeable layer 54 is at least higher than a lower edge of the air inlet 31. In a vertical direction, the permeable layer 54 may be completely located above the air inlet 31.

The air detection device 5 is located between the air inlet 31 and the fan 4. In this way, the air inlet 31 makes air flow obliquely toward the first boundary wall 3A after entering the air inlet 31. The inlet 41 of the fan 4 faces the second boundary wall 3B, and sequentially, air flows obliquely downward in at least a part of segments between the air detection device 5 and the inlet of the fan 4. The air flows obliquely upward and then flows obliquely downward between the air inlet 31 and the fan 4, and a part of the air may have potential energy of movement in the vertical direction when flowing through the gas sensor 51. Therefore, more air can be in contact with the sensing element 52 through the permeable layer 54, thereby helping improve detection accuracy of the gas sensor 51.

The first circuit board 50 is located in the air channel 3, a gap G1 is disposed between the first circuit board and the second lower boundary wall 3B of the air channel 3, and the gap G1 is closed at an upstream side of the first circuit board 50 adjacent to the air inlet 31, so that more air flows above the first circuit board 50 and flows through the gas sensor 51.

An air filter 62 between the air detection device 5 and the fan 4 may be disposed adjacent to the air detection device 5. The air filter 62 may be higher than the permeable layer 54.

In an embodiment, the air sanitation device 1 may include a carrying plate 7A located in the housing 2. The carrying plate 7A is located between the first housing 28 and the second housing 29. The air detection device 5 and the air purification device 6 are carried on the carrying plate 7A. The air channel 3 is located at a side of the carrying plate 7A on which the air detection device 5 and the air purification device 6 are mounted and defines a lower boundary of a corresponding segment of the air channel 3.

The fan 4 is supported by the carrying plate 7A, the inlet 41 of the fan 4 faces the carrying plate 7A, and a gap G2 is disposed between the inlet and an upper surface of the carrying plate 7A. The control unit 16 and the power supply unit 63 are fixed to a rear part of the carrying plate 7A.

The first circuit board 50 is fixed to the carrying plate 7A. The first circuit board 50 may be substantially parallel to the carrying plate 7A, and the gap G1 is disposed between a lower surface of the first circuit board and the upper surface of the carrying plate 7A. The gap G1 is closed by a closing portion 58 at the upstream side of the first circuit board 50, so that air cannot enter the gap G1.

Figure 6:
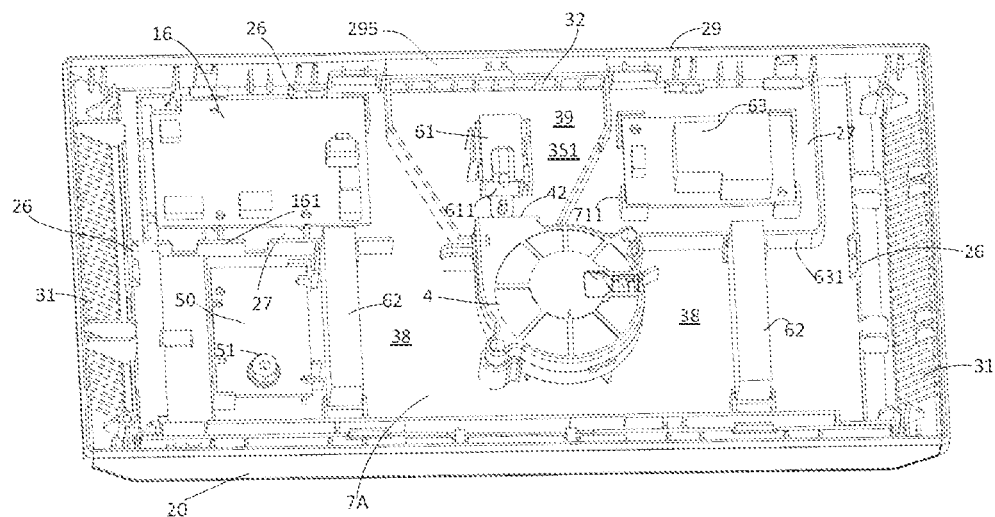
FIG. 6 is a three-dimensional view of the air sanitation device according to an embodiment of the present invention, where a first housing is removed.

As shown in FIG. 6, in an embodiment, the control unit 16 and the power supply unit 63 are disposed adjacent to a rear wall 22. The baffle walls 161 and 631 are respectively disposed around the control unit 16 and the power supply unit 63, to separate from the air channel 3.

Therefore, the air channel 3 extends transversely toward the middle from two sides of the housing 2, respectively, and then extends rearward after gathering in the fan 4. Therefore, air flows transversely in a front part of the housing 2 after entering the housing 2 from the two sides of the housing 2, flows toward the rear part of the housing 2 after entering the fan 4, and is discharged out of the housing 2, that is, returns to the storage compartment 101.

The outlet 42 of the fan 4 faces the air outlet 32 located at the rear part of the housing 2. The ion generator 61 is located between the outlet 42 and the air outlet 32. The outlet 42 of the fan 4 directly faces the ion generator 61.

As shown in FIG. 6, the second channel segment 39 may include an expansion segment 351 that is adjacent to the outlet 42 of the fan 4, and a width of which is gradually increased. Therefore, an end of the expansion segment adjacent to the outlet 42 of the fan 4 may have a smaller width, and in addition, the housing 2 still has an enough size for arranging the air outlet 32. This helps prevent corners that may trap air from being formed next to the outlet 42 of the fan 4, and in addition, the air outlet 32 distributed in a wider region helps air located downstream of the fan 4 be smoothly discharged out of the housing 2.

Figure 7:
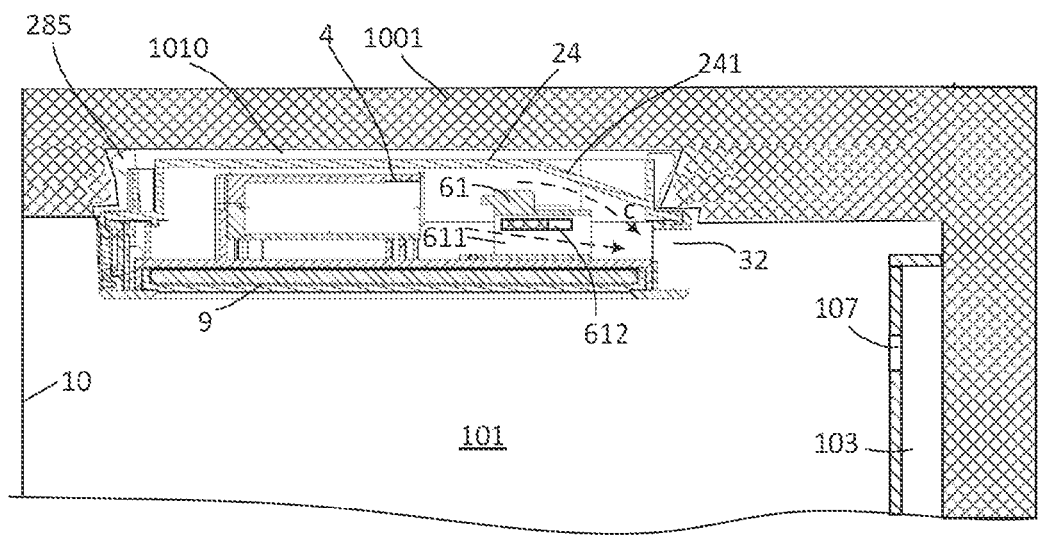
FIG. 7 is a schematic partial cross-sectional view of the refrigerator having the air sanitation device according to an embodiment of the present invention.
Figure 8:
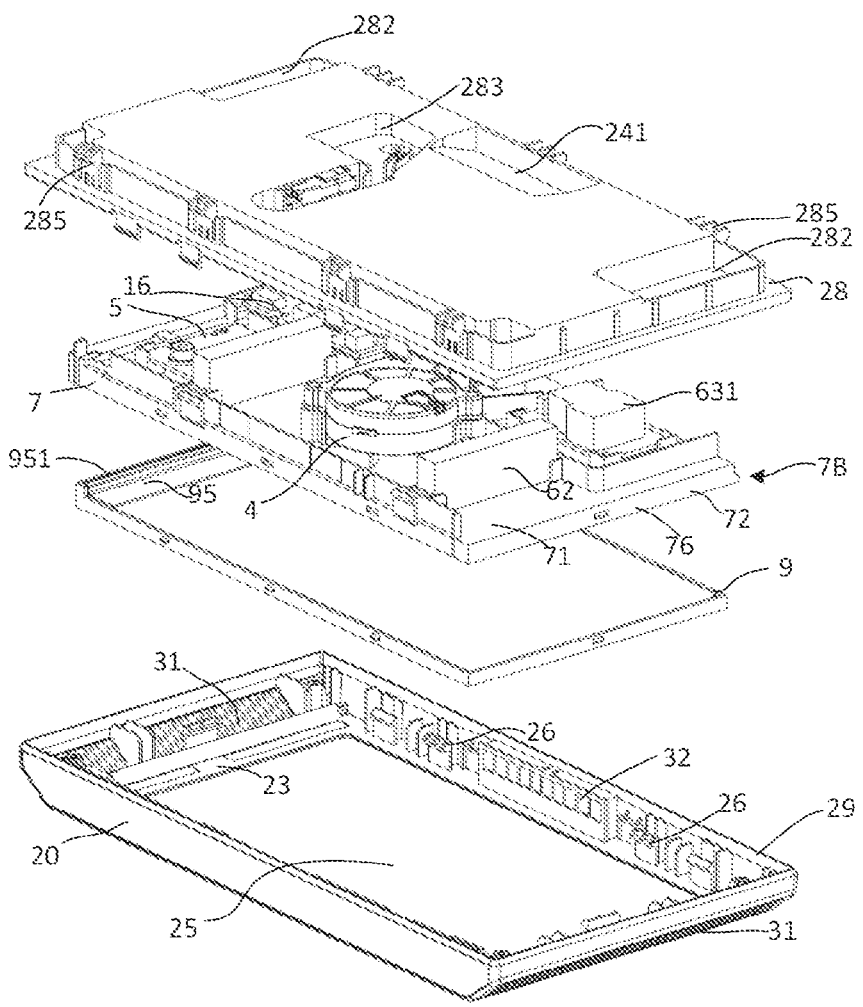
FIG. 8 is a schematic exploded, perspective view of the air sanitation device according to an embodiment of the present invention.

The ion generator 61 may be a point discharge ion generator. The ion generator 61 may also generate ozone by-products for sterilization when generating ions. Referring to FIG. 7 in combination with FIG. 6, the ion generator 61 may include a channel 611, and a tip ion generation component 612 is located in the channel 611. An inlet of the channel 611 faces the outlet 42 of the fan 4.

An outlet of the ion generator 61 may face the air outlet 32, so that products of the ion generator 61 may enter the storage compartment 101 through the air outlet 32 as rapidly as possible. The ion generator 61 may be disposed in such a way that the ions have a tendency to flow toward the air outlet 32.

As shown in FIG. 7, in an embodiment, the air channel 3 may disposed in such a way that at least a part of air is obliquely downward discharged out of the housing 2. Therefore, air including germicidal substances may flow obliquely downward, to further help the germicidal substances flow to other parts of the storage compartment 101. It is particularly advantageous that, the air flowing obliquely downward from the top part of the storage compartment 101 and including the germicidal substances may join airflow that is discharged from the air duct 103 located in the rear part of the storage compartment 101 and that flows forward, which helps the germicidal substances follow the airflow discharged from the air duct 103 to places where the forced air circulation passes.

As shown in FIG. 7, a depressed portion 1010 may be disposed in a top wall 1001, to mount the air sanitation device 1. In an embodiment, the upper wall 24 of the housing 2 is located in the depressed portion 1010 and defines an upper boundary of the air channel 3, and the air outlet 32 is located outside the depressed portion 1010. The upper wall 24 has a guiding portion 241 for guiding air downward to the air outlet 32, so that the air is guided to the air outlet 32 located outside the depressed portion 1010. On the one hand, this helps the air be accurately guided to the air outlet 32 and be smoothly discharged out of the housing 2. On the other hand, when the air is discharged out of the housing 2, at least a part of the air may be guided by the guiding portion 241 to flow obliquely downward toward the air outlet 32, so that at least a part of the air can flow obliquely downward.

The guiding portion 241 may include a slope that slopes from top to bottom. The slope may include a plane and/or a curved surface. A rear end of the guiding portion 241 may be connected to the rear wall 22 of the housing 2 provided with the air outlet 32. The rear end of the guiding portion 241 may be adjacent to the air outlet 32 and located above the air outlet 32.

A length of the guiding portion 241 may be greater than an entire length covering the ion generator 61 and cover the entire ion generator 61, so that air flows more smoothly toward the air outlet 32.

In an embodiment, the air sanitation device 1 includes the housing 2 provided with the air channel 3, and the air detection device 5 and/or the air purification device 6 located in the air channel 3. As shown in FIG. 4 and FIG. 5, the housing 2 includes a light outlet 25, the air sanitation device 1 includes an illumination device 9, and the illumination device 9 is located in the housing 2 to generate light adapted to pass through the light outlet 25. The light outlet 25 faces the storage compartment 101, to illuminate the storage compartment 101.

The light outlet 25 may be a through hole passing through the housing 2, or be formed through a light permeable wall of the housing 2.

The air sanitation device 1 includes a partition member 7, and the partition member 7 separates the illumination device 9 from the air channel 3, so that air is adapted to flow along a first side of the partition member 7, and the illumination device 9 is located between a second side of the partition member 7 and the light outlet 25.

By using the partition member 7 to separate the illumination device 9 from the air channel 3, air entering the housing 2 from outside may be separated from the illumination device 9, which particularly helps improve the service life of the air sanitation device 1 having the illumination device 9.

In an embodiment, the partition member 7 and the housing 2 together define an accommodating space 70 isolated from the air channel 3, and the illumination device 9 is located in the accommodating space 70.

When the air sanitation device 1 is arranged on the top part of the storage compartment 101, the air channel 3 having the air detection device 5 and/or the air purification device 6 is located above the illumination device 9. Both the accommodating space 70 and the air channel 3 may be in a flat structure. The accommodating space 70 may be distributed approximately parallel to the air channel 3.

The partition member 7 may include a carrying plate 7A for mounting the air detection device 5 and/or the air purification device 6. The air detection device 5 and/or the air purification device 6 may be fixed to the first side of the partition member 7. In an embodiment, the air detection device 5, the air purification device 6, and the fan 4 are mounted at the first side of the partition member 7 away from the light outlet 25. The control unit 16 and the power supply unit 63 may also be mounted at the first side of the partition member 7.

The partition member 7 and these electronic devices carried in the partition member 7 may be pre-assembled to form a pre-assembly module 7B.

The partition member 7 may include a main board portion 71 and a sideboard 72 extending from an edge of the main board portion 71 toward the light outlet 25. In this embodiment, the air sanitation device 1 is mounted on the top part of the storage compartment 101, the light outlet 25 is located at the bottom part of the housing 2, and the sideboard 72 extends downward from the main board portion 71.

The air detection device 5, the air purification device 6, and the fan 4 are mounted on the main board portion 71, so that the main board portion 71 forms the carrying plate 7A. The control unit 16 and the power supply unit 63 may also be mounted on the main board portion 71. The main board portion 71 may have a plurality of protrusions 711 protruding in a direction away from the light outlet 25, to fix these components.

A distal end of the sideboard 72 may overlap a lower wall 23 of the housing 2. The distal end of the sideboard 72 may overlap the lower wall 23 of the housing 2 by surrounding the light outlet 25. The air sanitation device 1 may include a first fixing mechanism configured to fix the partition member 7 to the housing 2. The first fixing mechanism may be configured to be adapted to generate a force that makes the distal end of the sideboard 72 tightly butt against the housing 2. This way helps reduce a probability that air enters the accommodating space 70 through a gap between the sideboard 72 and the housing 2.

The first fixing mechanism may include a plurality of hooks 26 disposed in the housing 2, and the hooks 26 are connected to the partition member 7 so that a force toward the lower wall 23 of the housing 2 is applied to the partition member 7. The hooks 26 may be distributed around the light outlet 25, and hook on an edge of the main board portion 71.

The illumination device 9 may be mounted at the second side of the partition member 7 facing the light outlet 25. In an embodiment, the main board portion 71 and the sideboard 72 enclose an accommodating cavity 701 opening toward the light outlet 25, and the illumination device 9 is at least partially located in the accommodating cavity 701. The accommodating cavity 701 may constitute at least main part of the accommodating space 70.

Figure 9:
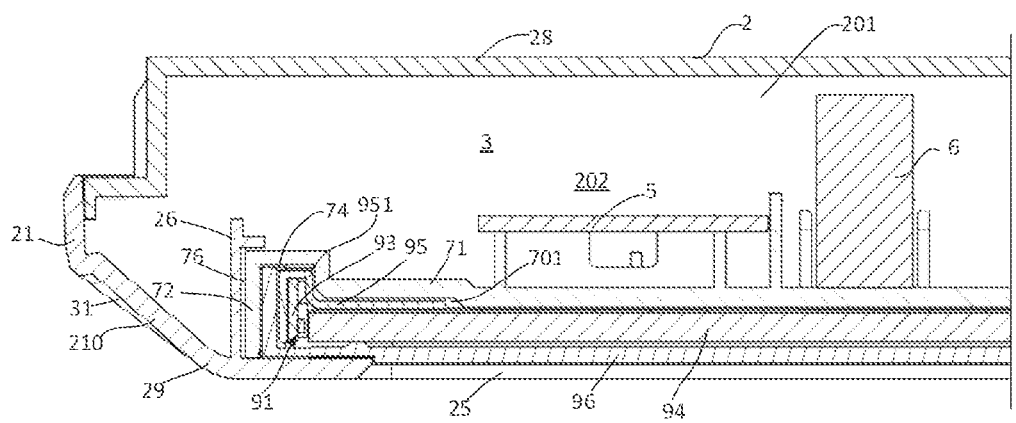
FIG. 9 is a schematic cross-sectional view of the air sanitation device according to an embodiment of the present invention.

As shown in FIG. 9, an illumination device 9 includes a light source 91. The light source 91 may include an LED light emitting element (not labeled) and a circuit board 93 carrying the light emitting element. In an embodiment, the circuit board 93 extends along a sideboard 72 and is located at a side in the accommodating cavity 701.

A partition member 7 may have a first slot 74 extending along the sideboard 72, and the circuit board 93 extends into the first slot 74. A depth of the first slot 74 is greater than depths of other parts of the accommodating cavity 701 in the partition member 7.

The illumination device 9 may include a light guide plate 94 and a frame bar 95 fixing the light source 91 to an end of the light guide plate 94.

The frame bar 95 has a protrusion 951 supporting the circuit board 93 and protruding toward the first slot 74, and the protrusion 951 extends into the first slot 74, so that the circuit board 93 also extends into the first slot 74.

The illumination device 9 may include a light diffuser 96. The light diffuser 96 covers an outer side of the light guide plate 94, and the light source 91 and the light guide plate 94 are located between a main board portion 71 and the light diffuser 96.

In an embodiment, the light diffuser 96 may be fixed to the partition member 7, so that the light source 91 and the light guide plate 94 are mounted in the accommodating cavity 701. For example, periphery of the light diffuser 96 may be connected to the sideboard 72 by buckles.

In an exemplary embodiment, the light diffuser 96 may be in a shallow tray shape opening toward the partition member 7, and the light source 91 and the light guide plate 94 are accommodated in the light diffuser 96.

The light source 91, the light guide plate 94, and the light diffuser 96 may be together mounted at the partition member 7 after forming a pre-assembly unit.

The light diffuser 96 is at least partially accommodated in the partition member 7. For example, a side wall of the light diffuser 96 is located in the accommodating cavity 701.

In an embodiment, a surface of the light diffuser 96 facing a light outlet 25 does not exceed a distal end surface of the sideboard 72.

The surface of the light diffuser 96 facing the light outlet 25 may be substantially flush with the distal end of the sideboard 72.

The partition member 7 has an end surface 76 adjacent to a side wall 21 having an air inlet 31, and the end surface 76 is exposed in the air channel 3. A gap is disposed between the end surface 76 and the side wall 21 of the housing 2. The side wall 21 has an oblique portion 210, an angle is disposed between the oblique portion and the end surface 76, and the air inlet 31 passes through the oblique portion 210. This can reduce occurrence of a case that the air entering the air channel 3 directly flows toward the end surface 76 and is blocked.

In an embodiment, the housing 2 includes a first housing 28 and a second housing 29, and the first housing 28 is connected to the second housing 29 to form a receiving space 201. The second housing member 29 has the light outlet 25. An accommodating space 70 for accommodating the illumination device 9 is formed between the partition member 7 and the second housing 29.

A second accommodating space 202 for accommodating an air detection device 5 and/or an air purification device 6 is disposed between the first housing 28 and the partition member 7. At least most of the air channel 3 is located between the first housing 28 and the partition member 7.

In an embodiment, the air inlet 31 is located in the second housing 29. The air inlet 31 may be at least partially lower than an upper surface of the main board portion 71 facing the first housing 28, and disposed obliquely so that air entering the air inlet 31 flows toward the first housing 28, thereby helping avoid a case that air entering the air channel 3 through the air inlet 31 is blocked by the partition member 7 and wind resistance is increased.

A lower edge of the air outlet 32 may be substantially flush with an upper surface of the partition member 7 facing the first housing 28, so that air flows to the air outlet 32 along the upper surface of the partition member 7.

The air outlet 32 may be disposed in the second housing 29. The second housing 29 may include a convex portion 295 protruding toward the partition member 7. An inner side of the convex portion 295 may be tightly adjacent to or be in contact with the side board 72 of the partition member 7 and the air outlet 32 is disposed on the convex portion 295, so that the air outlet 32 is tightly adjacent to the upper surface of the partition member 7, and air flowing along the upper surface of the partition member 7 can smoothly flow to the air outlet 32.

A first sunk part 282 may be disposed at rear ends of two sides of the first housing 28, to reduce air blown to the control unit 16 or the power supply unit 63. A second sunk part 283 may be further disposed in the first housing 28, to accommodate cables and terminals.

The air sanitation device 1 may be fixed in a depressed portion 1010 by using a plurality of hooks 285 located in the first housing 28.

Various embodiments illustrated with reference to FIG. 1 to FIG. 9 may be combined with each other in any given manner to realize the advantage of the present invention. In addition, the present invention is not limited to the shown embodiments. Usually, apart from the shown means, other means can also be used as long as the means can also achieve the same effect.

The invention claimed is:

1. An air sanitation device for a refrigerator, comprising:
   a housing;
   an air channel disposed in said housing and having an air inlet and an air outlet;
   a fan disposed in said air channel to force air to enter said air channel from said air inlet, and then be discharged out of said air channel from said air outlet, said fan having an inlet;
   an air detection device disposed between said air inlet and said inlet of said fan, wherein said air detection device has a circuit board and a gas sensor fixed to said circuit board;
   said air channel is configured to enable the air to flow along a side of said circuit board to which said gas sensor is fixed; and
   a direction that said inlet (41) of said fan (4) faces is opposite to a direction in which said gas sensor protrudes from said circuit board.

2. The air sanitation device according to claim 1, wherein:
   said housing has a pair of boundary walls disposed in opposite arrangement to define at least a part of said air channel;
   said gas sensor protrudes from said circuit board toward a first boundary wall of said pair of boundary walls; and
   said inlet of said fan faces a second boundary wall of said pair of boundary walls, and said gas sensor is closer to said first boundary wall than said inlet of said fan.

3. The air sanitation device according to claim 2, wherein:
said first boundary wall is disposed above said second boundary wall;
said gas sensor protrudes upward from said circuit board toward said first boundary wall;
said inlet of said fan faces downward toward said second boundary wall; and
said gas sensor has an upper end which is higher than said inlet of said fan.

4. An air sanitation device for a refrigerator, comprising:
a housing;
an air channel disposed in said housing and having an air inlet and an air outlet;
a fan disposed in said air channel to force air to enter said air channel from said air inlet, and then be discharged out of said air channel from said air outlet, said fan having an inlet; and
an air detection device disposed between said air inlet and said inlet of said fan, wherein said air detection device has a circuit board and a gas sensor fixed to said circuit board, said air detection device contains a cavity having an inlet, a permeable layer and said gas sensor enclosed in said cavity, said permeable layer covering said inlet of said cavity, and said permeable layer is higher than said inlet of said fan.

5. The air sanitation device according to claim 4, wherein said permeable layer is higher than at least a part of said air inlet.

6. An air sanitation device for a refrigerator, comprising:
a housing;
an air channel disposed in said housing and having an air inlet and an air outlet;
a fan disposed in said air channel to force air to enter said air channel from said air inlet, and then be discharged out of said air channel from said air outlet, said fan having an inlet;
an air detection device disposed between said air inlet and said inlet of said fan, wherein said air detection device has a circuit board and a gas sensor fixed to said circuit board, wherein said air detection device has a closing portion; and
a carrying plate disposed in said housing, said circuit board being fixed to said carrying plate, a gap is disposed between said circuit board and said carrying plate, and the gap is closed by said closing portion at an upstream side of said circuit board close to said air inlet.

7. The air sanitation device according to claim 1, wherein said housing has a first boundary wall and a second boundary wall in opposite arrangement to define an air channel, wherein said air detection device and/or said air purification device is fixed to said second boundary wall, and said air inlet is configured to enable the air to enter said air inlet and then flow obliquely toward said first boundary wall.

8. The air sanitation device according to claim 7, wherein said inlet of said fan faces said second boundary wall, so that the air flows obliquely downward at least in some segments between said air detection device and/or said air purification device and said inlet of said fan.

9. The air sanitation device according to claim 1, wherein said housing contains an upper wall, a lower wall, and a side wall, said side wall contains an oblique portion inclined downward, said air inlet is disposed on said oblique portion, and said inlet of said fan is open downward.

10. The air sanitation device according to claim 1, further comprising an air purification device containing:
an air filter disposed between said air inlet and said fan; and/or
a sterilization device disposed between said fan and said air outlet.

11. The air sanitation device according to claim 1,
further comprising a partition member and an illumination device disposed in said housing;
wherein said housing has a light outlet formed therein; and
wherein said air detection device is disposed at a first side of said partition member away from said light outlet, and said illumination device is located at a second side of said partition member facing said light outlet.

12. A refrigerator, comprising:
a storage compartment; and
the air sanitation device according to claim 1, said air sanitation device being disposed in said storage compartment.

13. The refrigerator according to claim 12, wherein:
said storage compartment has a top wall; and
said air sanitation device is fixed to said top wall of said storage compartment, said air channel is configured to enable the air to be discharged out from a rear part of said housing obliquely downward.

* * * * *